United States Patent [19]

Armengaud et al.

[11] Patent Number: 5,616,842
[45] Date of Patent: Apr. 1, 1997

[54] DEVICE FOR EVALUATION OF THE LUBRICATING CHARCTERISTICS OF A DRILLING MUD

[75] Inventors: Jean-Francois Armengaud, Toulouse; Alain Martignon, Oloron; Simeon Cortiade, Francon; Jacques Marti, Ibos, all of France

[73] Assignee: Elf Aquitaine Production, France

[21] Appl. No.: 502,640

[22] Filed: Jul. 14, 1995

[51] Int. Cl.$^6$ ..................................................... G01N 3/00
[52] U.S. Cl. ........................................ 73/152.18; 73/53.05
[58] Field of Search ............................ 73/53.05, 38, 151, 73/153, 154

[56] References Cited

U.S. PATENT DOCUMENTS

| | | | |
|---|---|---|---|
| 3,777,551 | 12/1973 | Weiss | 73/59 |
| 4,062,225 | 12/1977 | Murphy, Jr. et al. | 73/60 |
| 4,175,425 | 11/1979 | Brookfield | 73/59 |
| 4,341,115 | 7/1982 | Alekhin et al. | 73/153 |
| 4,557,142 | 12/1985 | Hensley et al. | 73/153 |
| 4,630,468 | 12/1986 | Sweet | 73/59 |
| 4,649,737 | 3/1987 | Joens | 73/38 |
| 4,799,382 | 1/1989 | Sprunt et al. | 73/153 |
| 5,052,219 | 10/1991 | Fery et al. | 73/153 |
| 5,325,723 | 7/1994 | Meadows et al. | 73/153 |

FOREIGN PATENT DOCUMENTS

| | | | |
|---|---|---|---|
| 1647364 | 5/1991 | U.S.S.R. | G01N 3/56 |
| 1772699 | 10/1992 | U.S.S.R. | G01N 19/04 |

Primary Examiner—Richard Chilcot
Assistant Examiner—Max H. Noori
Attorney, Agent, or Firm—Bacon & Thomas

[57] ABSTRACT

Device for evaluation of the lubricating characteristics of a drilling mud, including a vessel (14) provided with an entry (52) and an exit (58) for a mud to be analysed, a measuring shoe (40) mounted inside the vessel (14) and intended to be set in rotation, and at least one measuring sensor capable of measuring the stresses generated during a contact between the shoe and an internal surface of the vessel. According to the invention the sensor is mounted inside the shoe.

7 Claims, 2 Drawing Sheets

FIG_1

DEVICE FOR EVALUATION OF THE LUBRICATING CHARCTERISTICS OF A DRILLING MUD

BACKGROUND OF THE INVENTION

1. Field of the Invention

The present invention relates to a device for evaluation of the lubricating characteristics of a drilling mud.

During drilling for oil, mud under pressure is sent from the surface to the bottom of the well through the inside of the drill string and the mud then comes back up to the surface through the annular space defined between the string and the well wall.

The drilling mud is intended to lubricate and to cool the drilling tool which is driven in rotation at the bottom of the well. It is also used to bring the spoil back up to the surface. Finally, a function of the mud is to keep the well under pressure in order to prevent untimely arrivals of various components liable to be present under pressure in the well.

2. Description of Related Art

Drilling muds may be oil- or water-based. However, there is a tendency to replace oil muds, which had the advantage of having a high lubricating power, with water-based muds, for environmental reasons. It is appropriate, therefore, to improve the lubricating nature of a water-containing mud by adding additives to it. In order to have the ability to select the most suitable additives for improving the characteristics of a water mud, it is necessary to know its behaviour in the high pressure and high temperature conditions which prevail at the bottom of a wellbore.

The rock which surrounds a wellbore is generally porous, and as a result of this the liquid constituents of the mud tend to enter the rock, leaving solid particles to form a deposit on the well wall. The presence of this deposit of mud may be detrimental for the progress of the drilling, for two reasons. During the drilling it happens that the drill string, and more particularly the drill collars which are of larger diameter, come to rub against the well wall, where the presence of the mud deposit tends to brake the rotation of the string. This results in abrasion and overheating of the drill string and in higher energy consumption to keep the string in rotation. Moreover, when the string ceases to rotate for a prolonged period, it may happen that a phenomenon of jamming of a part of the string will occur in this mud deposit. In order to free the string, a certain traction force and a torque must be applied to it. An apparatus for analysing the lubricating characteristics of a drilling mud must make it possible to take these various phenomena into account, or even to reproduce them.

An apparatus intended to measure the force necessary to release a drill pipe previously jammed in a mud deposit created on an internal surface of the apparatus is known. The drill pipe is applied to the deposit with a force and for a period which are predetermined and the force needed to release the drill pipe is then measured. However, since the measuring sensors are arranged on the drill pipe outside the vessel of the apparatus, the friction produced on the drill pipe by the seal joints has a considerable effect on the measurements which are taken.

SUMMARY OF THE INVENTION

The subject of the present invention is therefore a device for evaluation of the lubricating characteristics of a drilling mud, which permits an increased accuracy of measurement while making it possible to recreate the temperature and pressure conditions existing at the bottom of wells.

To do this, the invention proposes a device for evaluation of the lubricating characteristics of a drilling mud, including a vessel provided with an entry and an exit for a mud to be analysed, a measuring shoe mounted inside the vessel and intended to be set in rotation, and at least one measuring sensor capable of measuring the stresses generated during a contact between the shoe and an internal surface of the vessel, characterized in that the sensor is mounted inside the shoe.

Other characteristics and advantages of the present invention will appear more clearly on reading the description which is given below, by way of example, with reference to the attached drawings.

DETAILED DESCRIPTION OF THE INVENTION

Figure 1:
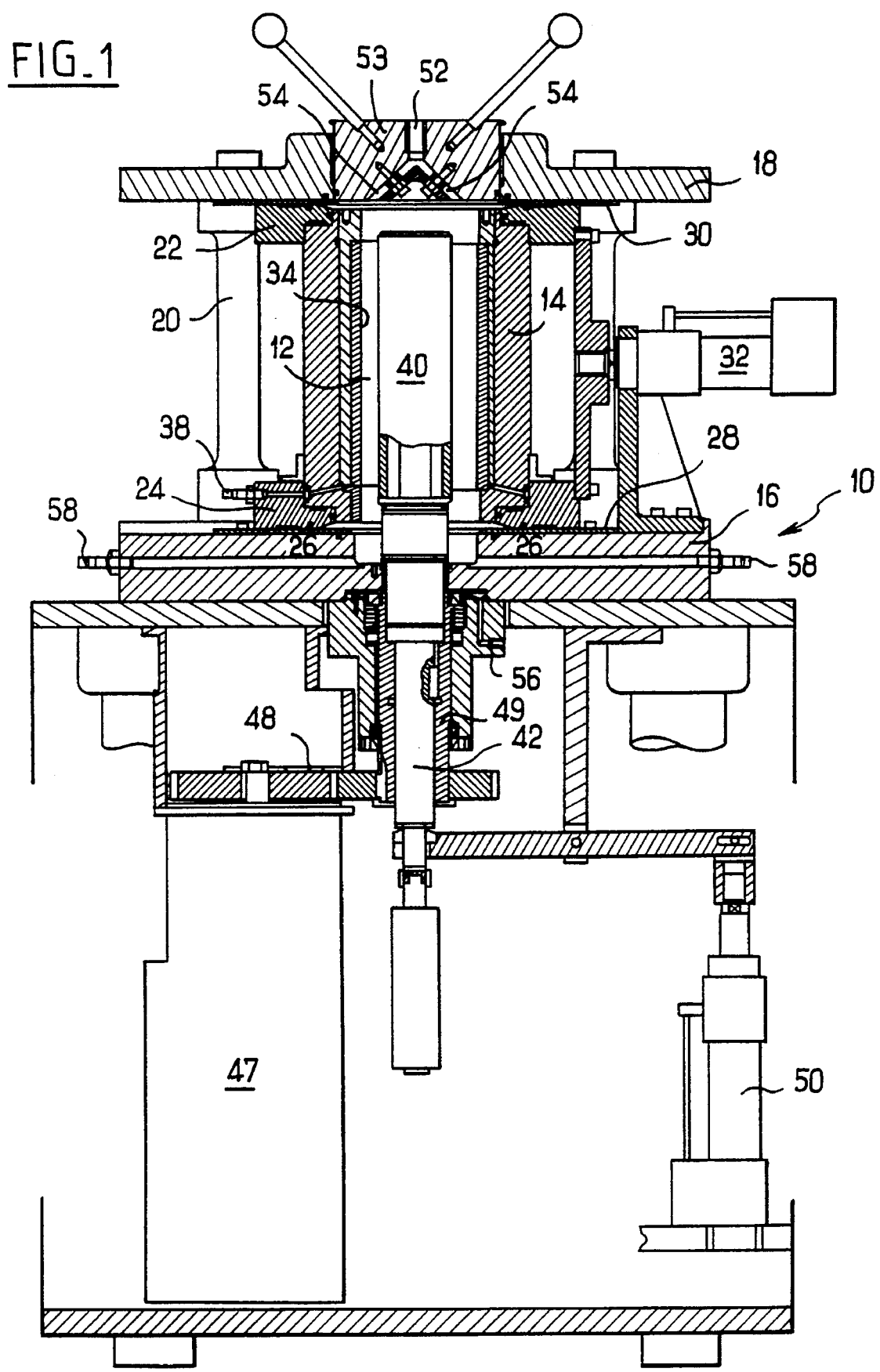
FIG. 1 is a general view, partially in lengthwise section, of a device for analysis according to the invention.
Figure 2:
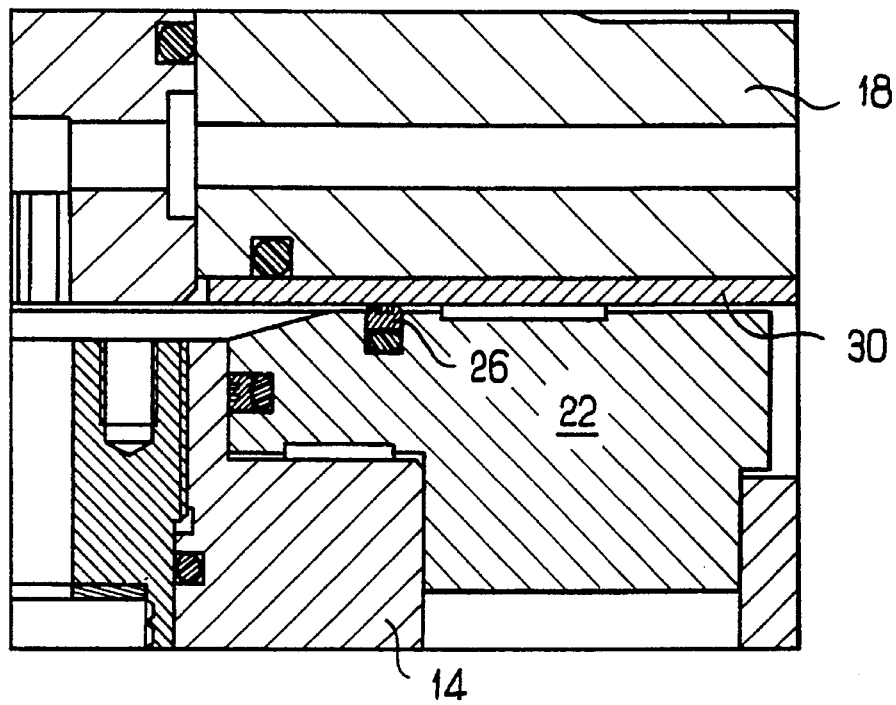
FIGS. 2 and 3 are detailed views of FIG. 1.

A device for evaluation which includes a measuring chamber 12 formed inside a vessel 14 is shown generally as 10 in FIG. 1. The vessel 14 is mounted between a lower flange 16 and an upper flange 18, mounted stationary on the lower flange 16 by means of columns 20 arranged symmetrically around the vessel 14. The vessel 14 is provided at each end with a radial collar 22, 24, each one comprising seal joints 26. These joints 26 ensure the leakproofing of the measuring chamber 12 by coming into intimate contact with two planar surfaces 28, 30 arranged on the lower support 16 and the lid 18 respectively (see FIG. 2).

The vessel 14 is intended to be moved, while maintaining the leakproofing of the chamber 12, between the lower flange 16 and the upper flange 18, under the effect of a jack 32. Inside the vessel 14 is mounted a pipe 34 made of porous material which is preferably a sintered material. The outer surface of the pipe 34 communicates with an exit 38.

A measuring shoe 40 is mounted in the chamber 12 on a shaft 42 which passes through the lower flange 16 in a leakproof manner. The shaft 42 is intended to be set in rotation by a motor 47 provided with gearing 48 by means of a sleeve 49 in which the shaft 42 is free to slide along its lengthwise axis. The measuring shoe 40 includes a steel cylinder fitted symmetrically onto the shaft 42. The shaft 42 is fitted, at its lower end, with a jack 50, offset in relation to the axis of the shaft 42 and intended to move the shaft 42, and thus the measuring shoe 40, along the lengthwise axis of the shaft 42.

The upper flange includes an entry 52 for mud to be analysed, defined in a removable closure member 53 which communicates with an orifice 54, of conical section, arranged to create a laminar flow of mud around the measuring shoe 40 and parallel to the axis of the shaft 42, towards an orifice 56 arranged in the lower flange 16, which is in communication with exits 58. The removable closure member 53 permits rapid cleaning of the apparatus.

According to the invention the sensor(s) intended to supply measurements as a function of the behaviour of the shoe 40 during the analytical experiments are arranged inside the shoe 40. The sensors are mounted on the internal surface of the shoe 40 and, in the example illustrated, are connected to a measuring centre by an electrical cable arranged inside the upper end (looking at the drawings) of the shaft 42 and by means of a rotating collector/sweeper unit (which are not shown). Other means can be employed for connecting the sensors to a measuring centre, for example an optical fibre cable or a radio transmitter-receiver unit. Among the sensors there is advantageously a sensor for the radial force applied to the shoe 40 and a resistance-torque sensor.

Figure 3:
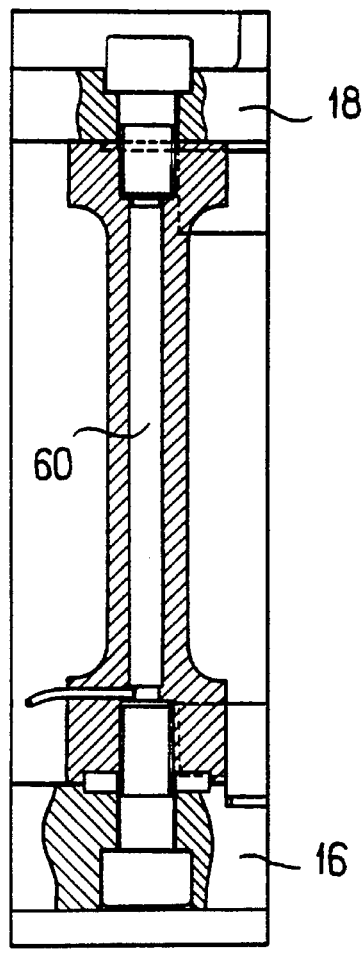

The device forming the subject of the invention is intended to be employed in the temperature and pressure conditions which prevail at the bottom of an oil well, where the temperature rises to approximately 150° C. The presence of fluid at such a temperature inside the chamber 12 creates a considerable temperature gradient across the vessel 14 and the collars 22, 24, and this can result in a physical distortion of the latter. This distortion would have the result of preventing the sliding of the vessel, under the effect of the jack, between the planar surfaces 28, 30. In order to ensure the free sliding of the vessel 14 between the planar surfaces 28, 30, the latter are provided with compound joints which, in the example illustrated, are made of cork/elastomer composite. This type of joint makes it possible to absorb the thermal expansion of the components and any possible manufacturing differences of the components. As shown in FIG. 3, and according to a second aspect of the invention, the columns 20 are adapted in order to keep the two planar surfaces 28, 30 parallel and for this purpose each one includes a heater element 60. Each heater element 60 includes an electrical resistor which is connected to a source of current by means of a rheostat (which are not shown). Thus, by varying the electrical current delivered to the resistor, it is possible to control the temperature of the columns in order to vary the length of the columns thermally. Since the columns 20 are arranged around the periphery of the planar surfaces 28, 30, these surfaces can be kept parallel by varying the length of the columns in order to ensure free sliding of the vessel 14.

The use of the device for analysis will now be described.

When the drilling mud flows at high temperature and pressure from the entry 52, through the interior of the chamber, towards the exit 58, a proportion of the liquid constituents of the mud passes through the porous pipe 34, under the effect of the differential pressure. The solid particles in this proportion of the mud lodge on the surface of the pipe 34. Having created this mud deposit from the mud to be analysed, it is possible to proceed with the analytical experiments.

The first type of experiment consists in evaluating the dynamic friction between the shoe and the mud deposit. In the presence of the mud the shoe 40 is set in rotation. Next, the jack 32 is actuated in order to move the porous pipe 14 and to bring the porous pipe 34, provided with the mud deposit, towards the shoe 40. The beginning of the entry of the shoe into the mud deposit is detected by measuring the radial force and the shoe is then driven by of the order of mm beyond this point into the mud deposit. From this moment on, measurements of the resistant torque and of the radial force are made. The experiment is repeated by moving the vessel 14 by means of the jack 32 in order to bring another region of the mud deposit into contact with the shoe 40.

The second type of experiment consists in evaluating the force and the torque which are necessary to release the shoe 40 once the latter is jammed in the mud deposit. To do this, in the presence of the mud whose circulation has been stopped, the vessel 14 is moved using the jack 32 in order to bring the porous pipe 34, provided with its mud deposit, into contact with the shoe 40. As in the preceding experiment, the beginning of the entry of the shoe 40 into the mud deposit is detected from measurements of the radial force and the shoe is then driven by of the order of mm beyond this point into the mud deposit. The rotation of the shoe is then stopped in order to cause the latter to jam in the mud deposit under the effect of the differential pressure which is applied to this deposit. From this moment on it is possible to measure the force necessary to release the shoe either by applying a torque or by moving the shoe along its lengthwise axis by actuating the jack 50. These experiments are repeated in the presence of a surfactant and then, as in the preceding example, the series of measurements is restarted by producing a contact between the opposite surface of the porous pipe and the shoe.

The dimensions of the device for evaluation are chosen in order to correspond to those of a drilling well. Thus, the internal diameter of the porous pipe is 15.25 cm and the external diameter of the shoe is either 8.9 cm or 12 cm. The axial length of the porous pipe is advantageously 30 cm. During the experiments, the mud circulates at a temperature of 150° C. and at a pressure of approximately 100 bars. The shoe is set in rotation at a speed similar to that of a drill string, that is to say of 0 to 150 revolutions/minute.

We claim:

1. Device for evaluation of the lubricating characteristics of a drilling mud, including a substantially tubular vessel provided with an entry and an exit for a mud to be analysed, said vessel being mounted so that it slides in a leakproof manner between a lower flange and an upper flange which are integrally attached to the device, a substantially cylindrical, rotatable measuring shoe mounted inside the vessel so that its lengthwise axis is substantially parallel to that of the vessel, means for moving the shoe along its lengthwise axis in relation to the vessel, and at least one measuring sensor mounted inside the shoe and capable of measuring the stresses generated during a contact between the shoe and an internal surface of the vessel.

2. Device according to claim 1, wherein it includes means intended to move the vessel in relation to the shoe in order to produce a contact between these latter parts.

3. Device according to claim 1 wherein the internal surface of the vessel is formed on a porous pipe arranged inside the vessel.

4. Device according to claim 1 wherein it additionally includes means for moving the vessel in relation to the shoe in order to make it possible to produce contact between the shoe and the internal surface of the vessel.

5. Device according to claim 1, wherein it includes means for varying the distance between the lower flange and the upper flange in order to ensure the free sliding of the vessel.

6. Device according to claim 5, wherein the means include columns connecting the lid to the lower support and comprising means for varying the length of the columns.

7. Device according to claim 6, characterized in that the means for varying the length of the columns include a heater element.

* * * * *